United States Patent [19]
Knapp

[11] Patent Number: 6,064,479
[45] Date of Patent: *May 16, 2000

[54] TWO PARAMETER VISUAL INSPECTION METHOD AND DEVICE

[76] Inventor: Julius Z. Knapp, 22 Foxwood Dr., Somerset, N.J. 08873

[*] Notice: This patent is subject to a terminal disclaimer.

[21] Appl. No.: 09/198,861

[22] Filed: Nov. 24, 1998

Related U.S. Application Data

[63] Continuation-in-part of application No. 08/714,232, Sep. 16, 1996, Pat. No. 5,940,176.

[51] Int. Cl.[7] .................................................. G01N 21/00
[52] U.S. Cl. ............................................. 356/240.1
[58] Field of Search ........................................... 356/240.1

[56] References Cited

U.S. PATENT DOCUMENTS

| | | | |
|---|---|---|---|
| 5,864,395 | 1/1999 | Laurberg | 356/427 |
| 5,940,176 | 8/1999 | Knapp | 356/240 |

*Primary Examiner*—Richard A. Rosenberger
*Attorney, Agent, or Firm*—Israel Nissenbaum

[57] ABSTRACT

A method and device for the accurate manual illumination inspection of transparent containers, such as pharmaceutically injectable vials, for particle contamination with light and dark particles. Opposing positioned and spaced first and second illumination sources are provided on opposite lateral sides of the container, with the container being positioned in an inspection volume at the illumination and physical midpoint (lumen light balance) between the illumination sources. A third illumination source with a diffusion screen is provided behind the inspection volume and container. Light from the opposing first and second light sources lateral to the container effects light reflection and scattering from white or light colored particles within the container and light from the third illumination source is visibly extinguished or blocked from reaching the inspector by black or dark colored particles. Prior art contrast inspections with light and dark colored backgrounds are effectively and more efficiently combined in a single illumination inspection without the use of such different contrast enhancing backgrounds.

16 Claims, 1 Drawing Sheet

FIG. 1
PRIOR ART
FIG. 2
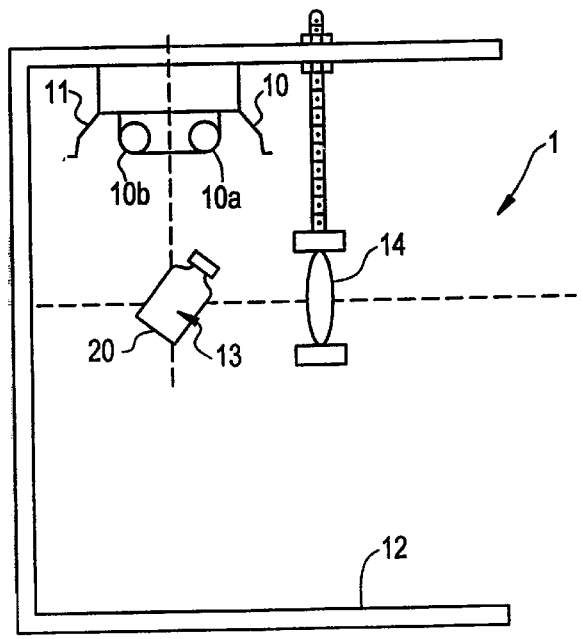
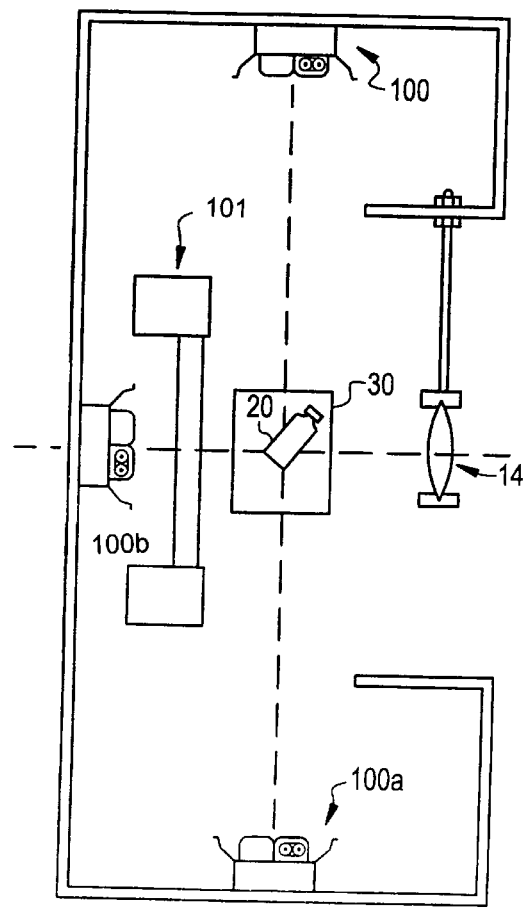

TWO PARAMETER VISUAL INSPECTION METHOD AND DEVICE

This is a continuation-in-part of my application Ser. No. 08/714,232 filed Sep. 16, 1996 now U.S. Pat. No. 5,940,176.

FIELD OF THE INVENTION

This invention relates to the inspection of uniformly illuminated three dimensional objects, and particularly to manual inspection of transparent objects such as vials, containing pharmaceutical injectables, for particle contamination with light and dark colored particles.

BACKGROUND OF THE INVENTION

The prior art manual inspection methodology for inspection of containers such as vials, containing pharmaceutical injectables, for particle contamination, involves a two step particle inspection sequence. The first step is the inspection of the container for black or dark particles in front of a flat white background which is used to optimize the contrast of black particles. The second inspection step occurs in front of a flat black background to improve the contrast and thus the detection for white or light colored particles. In both cases, the container is manipulated to induce motion in any suspended particles to permit the human eye to distinguish between stationary container defects and moving contaminating particles.

In prior art practice, the container is moved about 8 to 12 inches between the white and black background inspection locations. Repositioning the inspected container requires both refocusing of the eyes and accurate repositioning of the inspector's head and the inspected container for each part of the inspection since the container is inspected at a near focus position, approximately 10 inches from the eye. These wasted motions reduce the rate at which an inspection of acceptable quality can be achieved. The energy lost in these non-productive motions result in deteriorated inspection performance due to the cumulative effect of inspector fatigue and can reduce inspector efficiency by as much as 30% at the end of a full work day, especially when a magnifying lens is used in the inspection. Repositioning can also vary the illumination available for inspection of the container, thereby introducing additional variability in the results of the inspection.

Accordingly, in said prior patent application, the disclosure of which is incorporated herein by reference thereto, the black and white backgrounds, in an optional preferred embodiment, are integrated in a quick change structure to eliminate such lost energy and variability.

A light inspection booth used in the prior art manual inspection procedures for contaminating particles in pharmaceutical products, comprises a 60 Hz ballast which excites a pair of 20 watt 1½ inch diameter daylight fluorescent lamps arranged in an open lighting fixture above the inspection site. The prior patent application addresses improving the effect of lighting as used in the prior art, for enhancing inspection reliability.

The inspection for contaminating particles in injectable solutions has been shown to be probabilistic in nature, and with inspection performed with a fluorescent light source, a rough relationship between the probability of detecting a particle in a container and the particle size has been established.

In the standardized inspection conditions employed (without a magnifying lens), a 50 $\mu$m particle was not detected, a 100 $\mu$m particle was detected 70% of the time and a 200 $\mu$m particle was consistently detected 100% of the time. As the light intensity employed for the inspection is increased or the contrast of the particle increases, the detection probability is increased, with the corollary being that reduced light intensity and contrast results in decreased detection probability.

The target of the manual inspection therefore is the visible particle size range greater than 100 $\mu$m. The experimental rejection probability for all particles in this size range evaluates the effectiveness of the manual inspection. Extensive biophysics literature on human vision has established that the light intensity used for the inspection and the contrast of the target against the background determine both the rate and the accuracy with which a critical inspection can be successfully accomplished. Conversely, the wider the latitude of the illuminance employed for the inspection, the more variable will be the results of a manual inspection. With uncontrolled luminance variation the position of the inspected container with respect to the light source can multiply the difficulty of obtaining a secure inspection for contaminating particles.

With prior art light sources, the light intensity at the inspection point varies with the size of the inspected container and its position with respect to the light source. These factors modify the illuminance available for inspection of contaminating particles and thus the security with which these particles are detected.

To reduce the variability of human inspection results for contaminating particles in injectable fluids (or for that matter any type of similar illuminated inspection such as inspection for checking weld integrity and the like), the conditions under which the inspection is conducted must be defined and accurately controlled or contained.

The aforementioned co-pending application discloses a method and device for the accurate (with minimal variability) manual inspection of extended two dimensional surfaces or three-dimensional (not flat) samples, such as pharmaceutically injectable vials, for particle contamination, which samples are illuminated with diffused (non-point) light. Opposing vertically positioned and spaced illumination sources are provided above and below the sample, such as a vial, with the inspection volume (volume of the object, and movement space as may be required for inspection) being positioned at and around the illumination midpoint (lumen light balance) between the illumination sources for minimal illumination variability as a function of distance from the illumination midpoint. The position of the illumination mid-point for the inspection volume is adjustable according to the eye level of the particular inspector, whereby the illumination midpoint is brought into alignment with such eye level. Since the illumination midpoint, for light sources of equal intensity, is also the physical midpoint therebetween, adjustment is readily physically effected. Thus, lighting at any point and angle relative to the inspection volume (and in a plane parallel to the inspector) is possible, as long as the lighting is symmetrically balanced to provide the requisite illumination mid-point.

In order to further enhance inspection security and to reduce inspector fatigue there is no movement away from the designated inspection volume during any part of the inspection. Accordingly, the inspection is effected in front of a background which is automatically and quickly variable between light and dark to permit for optimal contrast for inspection for light and dark particles while the vial is at the inspection point within the inspection volume.

In prior art procedures, during the inspection against a white background, the contrast available for the detection of white particles is diminished. Similarly during the inspection against a black background, the contrast available for the detection of black particles is diminished. Detection benefits made possible by such procedures entail detection disabilities in 50% of the inspection for contaminating particles in injectable solutions.

By using the sequential test procedure described, inspectors can achieve a Reject Zone Efficiency (i.e., a reject rate of visible particle contaminated containers of about 85 to 90%). However, attempts to achieve inspection accuracy beyond this level result in an exponential increase in both real and false reject rates.

SUMMARY OF THE INVENTION

It is an object of the present invention to provide a lighting system for particle contamination inspection with improved Reject Zone efficiencies which reach 98%.

It is another object of the present invention to replace the sequential steps of contrast illumination of light and dark particles by means of dark and light backgrounds, with a single illumination step, with increased efficiency.

Generally the present invention comprises an effective inspection methodology and inspection station configuration which comprises the making available of the information from two contaminating particle description parameters in a single inspection station. The effect of the combination of the dual particle parameters is a vectorial combination of stimuli to the inspector. This results in a stronger particle signal to the inspector than with use of separate white and black background inspections.

The present invention comprises an inspection station with balanced lighting between opposing light sources lateral to an inspection volume with an object to be inspected for particle contamination positioned therein, as described in said prior patent application. The balanced lighting effectively provides a reflective detection means for light colored or white particles which are most reflective. In addition, the inspection station further comprises a non-glare (or diffused) light source which provides light in a direction from behind the inspection volume whereby light is blocked or extinguished primarily by dark particles for the facilitated detection thereof. As a result it is possible to obtain more reliable detection of all types of particles without the necessity for having or changing backgrounds to facilitate contrast. In accordance with the present invention particles are detected in a facilitated manner by means of the steps of:

a) determining and providing a detection volume for an object such as a vial containing an injectable solution with balanced light lateral (above and below or opposing sides) to the inspection volume for reflection or scattering of light from light or white colored particles in the solution when the particles are placed in motion within the vial; and b) simultaneously therewith providing diffused lighting from behind the inspection volume and towards an inspector for extinguishing or blocking of the light therefrom by dark colored particles as readily detected by an inspector.

In accordance with the present invention the two descriptive parameters which are utilized to effect inspections are the reflectivity of the particles and the light absorption characteristics of the particles. The combination of these two parameters into a single inspection station is achieved by selecting the delivery direction of three light sources with respect to the position of the inspector. Two light sources are positioned in a direction to deliver light to the inspected container so that only reflected or scattered light reaches the eyes of the inspector. The appearance of a particle which reflects light in the inspected volume (as defined in said prior application as being a volume with a selected minimal variation in illumination over the entire volume of the container) is determined as an instantaneous increase of the background illumination. Light colored or white particles produce the strongest reflective signals with a suitable light for such purpose being the opposing balanced lighting of said co-pending application (such opposed balanced lighting being referred to hereinafter as the first and second light sources).

The third light source delivers light directly in the direction of the inspector, i.e., as a form of "backlighting". With such lighting the appearance of a particle that absorbs or blocks light in the inspected volume of the container is determined as an instantaneous decrease of the background illumination. Opaque, dark colored or black particles produce the strongest light absorbing signals. A translucent diffusion panel at least equal in size to the cross-section of the accurately defined light intensity inspection volume, parallel to the inspector, delivers light from the direct source to the inspection volume.

The light intensity of the source is adjusted to obtain securely detectable contrast from opaque white and black particles, with a typical operating intensity for the direct light source being up to about 50% and preferably between 10 to 50% of the light intensity delivered by a single fluorescent light fixture (preferably depending upon standard light intensities units commercially available).

The above and other objects, features and advantages of the present invention will become more evident from the following discussion and drawings.

SHORT DESCRIPTION OF THE DRAWINGS

FIG. 1 is a schematic rendering of an inspection station of the prior art as currently used; and FIG. 2 is a schematic rendering of the inspection station of the co-pending application as modified in accordance with the present invention showing the positioning of the light sources relative to an inspection volume and an inspector.

DETAILED DESCRIPTION OF THE INVENTION

Generally the present invention comprises a method and device for the accurate (with minimal variability) manual inspection of extended two dimensional surfaces or three-dimensional (not flat) samples, such as pharmaceutically injectable vials, for particle contamination, which samples are illuminated with diffused (non-point) light. With respect to the first light source which provides the source of the scattered or reflected light, opposing vertically positioned and spaced illumination sources are provided above and below the sample, such as a vial, with the inspection volume (volume of the object, and movement space as may be required for inspection) being positioned at and around the illumination midpoint (lumen light balance) between the illumination sources for minimal illumination variability as a function of distance from the illumination midpoint. The position of the illumination mid-point for the inspection volume is adjustable according to the eye level of the particular inspector, whereby the illumination midpoint is brought into alignment with such eye level. Since the illumination midpoint, for light sources of equal intensity, is also the physical midpoint therebetween, adjustment is readily physically effected. The adaptation of existing manual stations with lighting below the inspection volume is not to be construed as limiting. Thus, lighting at any point and angle relative to the inspection volume (and in a plane parallel to the inspector) is possible, as long as the lighting is symmetrically balanced to provide the requisite illumination mid-point, with the ultimate illuminated inspection station comprising a balanced series of lights positioned in a circle about the inspection volume. Similarly though the present invention is illustrated with respect to manual inspections, equivalent machine inspections which are dependent on minimized illumination variations are similarly within the purview of the present invention.

Though the mid-point is not the location of maximum illumination for the light sources employed, normal variation in manual inspections, e.g., variations in inspector height and deviations caused by manual handling of the vial, at the mid-point, result in minimal deviations in illumination, with resulting greater accuracy and replicability of inspection results. The mid-point illumination should however be of adequate recommended inspection intensity since it is normally the point of least illumination intensity. Accordingly the multiple light sources should be preselected to provide recommended illumination levels at the inspection midpoints.

In order to further enhance inspection security and to reduce inspector fatigue, it is preferred that there be no movement away from the designated inspection volume during any part of the inspection.

DETAILED DESCRIPTION OF THE DRAWINGS AND THE PREFERRED EMBODIMENT

A prior art light inspection booth or station 1 used in the prior art manual inspection procedures, for detection of contaminating particles in pharmaceutical products, typically has a single light source 10. The light source consists of a 60 Hz. ballast that excites a pair of 20 watt 1½ inch diameter daylight fluorescent lamps, 10a and 10b. The fluorescent lamps are positioned in an open lighting fixture 11 which is mounted 20 inches above the work surface 12 and about 8 inches from the inspection point 13. The booth can be used with or without a magnifying lens 14. The lamp wattage, the distance from the lamps to the inspected container 20, and the 225 foot-candle illuminance produced by this light source for the inspection are based on the Illumination Engineering Society of North America recommendations.

Movement away from a light source 10 reduces the light intensity received from that source. However, as shown in FIG. 2, and as shown in detail in said prior application, a compensation mechanism to maintain constant light intensity can be realized when two light sources 100 and 100a are arranged in a line pair and directed toward each other. Any such combination results in less variation of lighting intensity in the inspection volume than the single light source, which is in present use.

Accurate control of inspection light intensity for the use in the inspection or measurement of flat objects, or for the measurement of dimensions that are measured in a single plane, is readily effected. The object to be examined is simply inspected at a specified distance in front of a uniformly lighted panel.

However, accurate inspections for particulate contamination of the contents of transparent containers 20 filled with injectable pharmaceutical products require the use of a uniformly lighted volume (inspection volume) 30 rather than a single plane. The volume requirements are based on the physical size of the container plus the volume required to enclose the space in which container movement is effected, to impart motion to the suspended particles. Particle motion is required to provide the inspector with a means to differentiate contaminating particles within the liquid from optical container flaws and surface dirt on the container. The maintenance of accurate light intensity is also important in the high speed automated inspection of three dimensional objects.

The ideal light source for development of a volume of constant illumination is a light source with a linear variation of light intensity at a distance from the source. With such an ideal source available, a constant illumination volume can be realized between a line-pair of such light sources. The line-pair arrangement consists of a pair of parallel, inward facing lamps mounted as if on opposite equal faces of a rectangular parallelepiped corresponding to the size of the lamps in their fixture. On the line between the equal light sources, movement away from one source, with its attendant loss of light intensity, is completely compensated by the increased intensity available from the corresponding movement to the second light source of the pair. Thus, with constantly maintained illumination between the light sources at all points between the light sources, movement in an inspection volume provides neither variation in illumination nor any variation in inspection security.

However, the variation of light intensity from a practical light source is not linear with distance. All real or practical light sources (e.g. lights 100 and 100a in FIG. 2) have a non linear relationship between their delivered light intensity and the distance from the light source. With these light sources, there is no distance from a single light source around which an even, symmetrical function of light intensity, $f(x)=f(-x)$ and distance can be developed since these practical light sources are odd functions of light intensity and distance.

Optimum symmetry with practical light sources (e.g., a fluorescent light source as in the prior art) is at the mid-point 50 between the light sources where the light delivered from each source is equal. However, at this mid point, the total illumination is at a minimum and any departure from this equidistant point between the light sources actually increases the inspection point illumination.

The recent availability of improved fluorescent lamps that maintain their initial light intensity within 10% for 10,000 hours has made possible an improved, more accurate, inspection lighting method. These new 16 mm folded fluorescent lamps use improved, better balanced, 4100° Kelvin daylight phosphors (GE F40/30BX/SPX/41 RS or its Phillips equivalent PL-L 4OW/30RS/41). Operated with high frequency electronic ballasts at 20 KHz they provide both flicker-free illumination and reduced light fixture heat. Both are important factors in minimization of inspector fatigue. The fluorescent lamps are hairpin shapes 16 mm in diameter lamps 22½ inches (527 mm) long. The 40 watt Phillips PL-L 40w/30 RS with the 4100° K color temperature or the G. E. equivalent are particularly suited for this type of inspection use. An open luminaire for two of these lamps mounted with all lamp tubes parallel to the backplane is equipped with 1½ inch wide by 2 inch high symmetrical channel reflectors on each side of the channel light fixture. To ensure freedom from end effect variation, the lighting zone used for inspection is limited to the central ⅔ of the lamps (approximately 14 inches). This provides a 12 inch deep X 14 inch long constant intensity lighting zone area. The height of the inspection volume is determined by the distance from the lamp surface in which the magnitude and variability of the light intensity are determined to be within design limits.

A design for a constant light intensity volume that uses the illumination balance of the present invention, between an inward directed pair of lights must consider both the requirement for a constant intensity light source and the light source power required to deliver the specific level of light intensity required. The closer a selected operating mid-point is to the light source, the higher the light intensity and the steeper the variation of light intensity with distance from the source. The result of this relationship is that increasing the distance from the light sources to the center-point between the lights, increases the volume within which the light intensity is linearized. The increased volume within which lighting accuracy has been maintained is achieved at the price of a lower light intensity level. Accurate maintenance of the light intensity within a volume and the intensity of the illumination achieved are linked problems. The maintenance of light intensity and the delivery of a required level of light intensity is accomplished by increasing the available light source intensity and thus the power of the source.

The dimensions of the inspection volume for the inspection of injectable pharmaceutical products is related to the size of the containers to be inspected for contaminating particles. The height range of the inspected container for Small Volume Injectables, those with injectable volumes below 100 ml, varies from approximately 1½ to 4½ inches to as much as 9 inches for Large Volume Injectables. A 6 inch high inspection volume, in which light is accurately maintained, provides adequate volume for the particle contamination inspection of Small Volume Injectable containers up to 3 inches in height. The height of the inspection volume must include an allowance for the manual movements of the container during the inspection. A 9 inch high inspection volume should be adequate to inspect the full range of Small Volume Injectable containers (containers with volumes up to 100 ml and up to 4½ inches in height). A similar height margin for the inspection of Large Volume Injectables results in a 12 inch high inspection volume to accommodate the manual inspection movements of the larger container size (containers between 250 ml and 1 liter).

Either direction of movement from the centerpoint results in an increase of illuminance and an increase in the variability of illuminance intensity available for the manual inspection process. For movement from the center point that is large enough, the total illuminance available for inspection approaches that of the single light source. Any use of an inward directed lighting arrangement reduces the illuminance variability of a single lamp source for inspection. The greatest improvement results when equal intensity light sources are employed and the centerpoint of the inspection volume coincides with the point at which the light intensity from each source is equal i.e. at the midpoint between them. Any departure from symmetry reduces the illuminance linearized volume obtained with full symmetry.

Lights 100 and 100a, laterally (relative to the inspector) and opposingly positioned around the inspection volume effectively provide the requisite light for reflection and/or scattering primarily by white or light colored particles at least equivalent to the use of a black or dark background to provide contrast to aid in inspector recognition. Light 100b is positioned behind the inspection volume together with a diffusion screen 101 (which permits use of any lighting source. Fluorescent lights similar to those used in light sources 100 and 110a is however preferred) with diffused light being directed through the container 20 towards the inspector (other diffusion means may be effectively utillized). The intensity of light 100b is up to 50% that of either of lights 100 and 100a (in a presently used station of about 375 foot-candles, light 100b is accordingly preferably up to about 200 foot-candles in intensity).

Light from light 100b is recognizably blocked or extinguished primarily by black or dark colored particles thereby effectively providing a contrast recognition by inspectors in place of a light background. Thus, both light and dark colored particle are reliably and efficiently detectable in a single inspection step with detection reliability of up to 98% without problems inherent with multiple colored background inspections.

It is understood that the above discussion, drawings and specific examples are illustrative of the present invention and that changes may be made in structure, components, relative relationships, method steps and the like without departing from the scope of the present invention as defined in the following claims. Thus, method and inspection station may have similar utility with optical machine based inspection systems and with respect to machine vision magnification systems in place of optical lenses.

What is claimed is:

1. A method for enhancing the reliability of an illuminated inspection of light and dark colored particles in a container in an inspection station wherein the inspection station comprises a first illumination source positioned on one side of an inspection volume in which the container is positioned, and which inspection volume is visually aligned with an inspector for inspection with illumination from the first illumination source; said method comprising the steps of:

a) providing a second illumination source on a second side of the inspection volume substantially directly opposite that of the first illumination source and substantially in line therewith;

b) substantially visually aligning the inspection volume with an illumination midpoint between the first illumination source positioned on one side of the inspection volume and the second illumination source positioned on the side substantially opposite to the first illumination source relative to the inspection volume;

c) providing a third illumination source behind the inspection volume relative to an inspector;

d) directly illuminating the container with the respective illumination sources whereby the light from the first and second illumination sources is detectably reflected and scattered by light colored particles within the container and wherein light from the third illumination source is detectably blocked and extinguished by dark colored particles.

2. The method of claim 1, wherein additional illumination sources are positioned around the illumination midpoint with illumination symmetry.

3. The method of claim 1, wherein the inspection is visually conducted by a human.

4. The method of claim 1 wherein the inspection is conducted with the optical input of a machine vision system.

5. The method of claim 1, wherein the inspection volume includes a volume to contain movement of the container to place particles, which may be contained therein, into motion.

6. The method of claim 1, wherein the distance between the first and second respective light sources is at least 20 inches and wherein illumination intensity from the first and second light sources at the inspection volume is at least 250 foot-candles and from the third light source is upt to about 200 foot-candles.

7. The method of claim 1, wherein both first and second light sources are of substantially equal intensity and wherein the inspection volume is located substantially at the physical midpoint between the respective first and second light sources.

8. The method claim 1, wherein light diffusion means is positioned between the third light source and the container.

9. An inspection station for illuminated inspection of transparent containers having injectable solutions with light and dark colored particles therein, with enhanced reliability, wherein the inspection station comprises a first illumination source positioned on one side of an inspection volume in which the container is positioned, and which inspection volume is visually aligned with an inspector for human inspection with illumination from the first illumination source; wherein the inspection station further comprises a second illumination source on a second side of the inspection volume substantially directly opposite that of the first illumination source and substantially in line therewith; wherein the inspection volume is substantially aligned with an illumination midpoint between the first illumination source positioned on one side of the inspection volume and the second illumination source positioned on the side substantially opposite to the first illumination source relative to the inspection volume; and wherein a third illumination source and means for diffusion of light therefrom are positioned behind the inspection volume, relative to the inspector; whereby there is direct illumination of the contents of the container by the respective three illumination sources only with light therefrom which is in a substantially direct line between the respective first and second illumination sources and between the third illumination source and the inspector.

10. The inspection station of claim 9, wherein additional illumination sources are positioned around the illumination midpoint with illumination symmetry.

11. The inspection station of claim 9, wherein the inspection volume includes a volume to contain movement of the containers to place particles, which may be contained therein, into motion.

12. The inspection station of claim 9, wherein the distance between the respective light sources is at least 20 inches and wherein illumination intensity from the first and second light sources at the inspection volume is at least 250 foot-candles and the illumination intensity from the third light source is up to about 200 foot-candles.

13. The inspection station of claim 9, wherein the first and second light sources are of substantially equal intensity and wherein the inspection volume is located substantially at the physical midpoint between the respective light sources.

14. The inspection station of claim 9, wherein a magnifying lens is interposed between the inspector and the inspection volume.

15. The inspection station of claim 9, wherein a machine vision magnification system is interposed between the inspector and the inspection volume.

16. The inspection station of claim 9, wherein the third light source is one of a point and incandescent light and said diffusion means is a translucent diffusion screen.

* * * * *